(12) United States Patent
Liu et al.

(10) Patent No.: US 7,696,488 B2
(45) Date of Patent: Apr. 13, 2010

(54) IRRADIATING DEVICE AND METHOD FOR CONTROLLING THE SAME

(75) Inventors: Yaohong Liu, Beijing (CN); Huaping Tang, Beijing (CN); Xinshui Yan, Beijing (CN); Jianjun Gao, Beijing (CN); Feng Gao, Beijing (CN); Dongsheng Zhang, Beijing (CN); Xiaotian Liang, Beijing (CN); De Wei, Beijing (CN); Jinsheng Liu, Beijing (CN); Wei Jia, Beijing (CN); Wei Yin, Beijing (CN); Dan Zhang, Beijing (CN); Chong Gu, Beijing (CN); Qinghui Zhang, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 232 days.

(21) Appl. No.: 11/778,955

(22) Filed: Jul. 17, 2007

(65) Prior Publication Data

US 2008/0067406 A1    Mar. 20, 2008

(30) Foreign Application Priority Data

Jul. 17, 2006    (CN) .................... 2006 1 0098857

(51) Int. Cl.
| | |
|---|---|
| G01K 1/08 | (2006.01) |
| H01J 3/14 | (2006.01) |
| H01J 3/26 | (2006.01) |
| H01J 49/42 | (2006.01) |
| H01J 5/18 | (2006.01) |
| H01J 35/18 | (2006.01) |
| H01J 35/30 | (2006.01) |
| G02B 5/00 | (2006.01) |
| G21K 1/00 | (2006.01) |
| A61N 5/00 | (2006.01) |
| G21G 5/00 | (2006.01) |

(52) U.S. Cl. .................... 250/399; 250/398; 250/396 R; 250/505.1; 250/492.3; 378/137; 378/140

(58) Field of Classification Search ............. 250/396 R, 250/398, 399, 505.1, 492.3; 378/121, 137–139, 378/64, 140, 148, 158

See application file for complete search history.

(56) References Cited

U.S. PATENT DOCUMENTS 2,993,120 A * 7/1961 Emannelson .............. 250/492.3

(Continued)

FOREIGN PATENT DOCUMENTS

JP    07051395 A * 2/1995

(Continued)

*Primary Examiner*—Jack I Berman
*Assistant Examiner*—Brooke Purinton
(74) *Attorney, Agent, or Firm*—Price, Heneveld, Cooper, DeWitt & Litton, LLP

(57) ABSTRACT

An irradiating device and a method for controlling it are provided. The device comprises an electron accelerator and a scanning box connected to the electron accelerator, wherein the scanning box is provided with a target, an electron beam exit window positioned at left or right side of the target and a scanning magnet. The device integrates the functions of both the existing irradiating device outputting electron beams and those outputting X-rays. When the scanning magnet is in operation, the irradiating device outputs electron beams; and when the scanning magnet is not in operation, the irradiating device outputs X-rays. Therefore, the device is capable of outputting two radiation sources so as to meet requirements for radiation-processing articles with different sizes.

9 Claims, 3 Drawing Sheets

U.S. PATENT DOCUMENTS

| | | | | |
|---|---|---|---|---|
| 3,013,154 A | * | 12/1961 | Trump | 250/398 |
| 3,158,745 A | * | 11/1964 | Stanhope | 250/399 |
| 3,176,137 A | * | 3/1965 | Helmut et al. | 250/399 |
| 3,287,584 A | * | 11/1966 | Pinel | 250/398 |
| 3,398,307 A | * | 8/1968 | Brown et al. | 250/399 |
| 3,676,673 A | * | 7/1972 | Coleman | 250/398 |
| 3,780,305 A | * | 12/1973 | Free | 250/398 |
| 3,876,373 A | * | 4/1975 | Glyptis | 422/23 |
| 3,902,097 A | * | 8/1975 | Offermann | 313/420 |
| 4,075,496 A | * | 2/1978 | Uehara | 250/396 ML |
| 4,159,436 A | * | 6/1979 | Ely | 250/398 |
| 4,295,048 A | * | 10/1981 | Cleland et al. | 250/398 |
| 4,484,341 A | * | 11/1984 | Luniewski | 250/399 |
| 4,726,046 A | * | 2/1988 | Nunan | 250/492.3 |
| 4,845,370 A | * | 7/1989 | Thompson et al. | 250/398 |
| 5,401,973 A | * | 3/1995 | McKeown et al. | 250/396 R |
| 5,461,656 A | * | 10/1995 | Golovanivsky et al. | 378/66 |
| 5,847,401 A | * | 12/1998 | McKeown et al. | 250/396 ML |
| 6,113,851 A | * | 9/2000 | Soloshenko et al. | 250/492.1 |
| 6,180,951 B1 | * | 1/2001 | Joehnk et al. | 250/492.3 |
| 6,327,339 B1 | * | 12/2001 | Chung et al. | 250/505.1 |
| 6,628,750 B1 | * | 9/2003 | Korenev | 378/64 |
| 6,653,641 B2 | * | 11/2003 | Lyons et al. | 250/492.2 |
| 6,683,319 B1 | * | 1/2004 | Koenck et al. | 250/396 R |
| 7,067,822 B2 | * | 6/2006 | Lyons et al. | 250/435 |
| 7,133,493 B2 | * | 11/2006 | Avnery | 378/140 |
| 2003/0089862 A1 | * | 5/2003 | Jongen | 250/492.3 |
| 2005/0230640 A1 | * | 10/2005 | Loda et al. | 250/492.3 |
| 2006/0256925 A1 | * | 11/2006 | Virshup et al. | 378/158 |

FOREIGN PATENT DOCUMENTS

JP    2003079753 A  *  3/2003

* cited by examiner

IRRADIATING DEVICE AND METHOD FOR CONTROLLING THE SAME

BACKGROUND OF THE INVENTION

1. Field of the Invention

The invention generally relates to an irradiating device in the art of radiation processing, and a method for controlling the same.

2. Description of Related Art

Radiation processing is now used to prepare macromolecular materials, keep foods fresh, sterilize medical products and drugs, protect products from contaminating, color crystals and pearls, and treat environmental contaminants with high energy electron beams, X-ray generated by a target hit by electron beams or Gamma ray radiated by a radionuclide. The radiation processing, as an economic, energy saving, manpower saving and harmless new processing method, is widely applied to various fields such as agriculture, industry and medicine, and becomes increasingly important.

Generally, high energy electron beams are generated by accelerators such as traveling or standing wave linear accelerators, and DC high voltage accelerators, which further include static accelerators, transformer type accelerators with insulating core, electron curtain accelerators, high frequency and high voltage accelerators, etc. As shown in FIG. 1, an irradiating device outputting electron beams comprises an electron linear accelerator 1, a scanning magnet 3 mounted on the electron linear accelerator 1 via a flange 2, and a scanning box 4 of triangle shape. The scanning box 4 is provided with an electron beam exit window 10 right in a direction of electron beams output from the electron linear accelerator, and a cooling fluid loop 9 at the bottom of the scanning box 4 for cooling the electron beam exit window 10. The cooling fluid loop 9 is externally connected to a cooling fluid system via an inlet 8 and an outlet 12. In operation, the scanning magnet 3 scans in bidirectional mode, that is, a positive current and a negative scanning current are respectively supplied to the scanning magnet 3 for half of a scanning period. The irradiating device configured in this way typically directs electron beams 5 through scanning box 4, and then carries out radiation processing. Although radiation processing with electron beams has advantages of great power, high efficiency, excellent safety and so on, it could only be used for small or thin articles due to the low processing depth of electron beams. It is not suitable for processing big articles that cannot be separated into smaller ones, such as logs to be cleared of pests. Furthermore, the scanning boxes of the conventional electron beam exit window type irradiating devices are required to have scanning magnets with good stability. If the scanning magnet 3 fails in operation, even for a very short time, the electron beams 5 would damage the electron beam exit window 10 greatly, and even damage the entire system including the electron linear accelerator 1 and the scanning box 4.

Therefore, an irradiating device outputting X-rays is typically used to irradiate big articles that cannot be separated into smaller ones. As shown in FIG. 2, such irradiating device outputting X-rays comprises an electron linear accelerator 1, a shift section 13 mounted on the electron linear accelerator 1 via a flange 2, a target 7 mounted at a center of the outputting beams, and a cooling fluid loop 9 at bottom of the shift section 13 for cooling the target 7. The cooling fluid loop 9 is externally connected to a cooling fluid system via an inlet 8 and an outlet 12. The radiation processing is carried out utilizing X-rays generated by the target hit by the electron beams originated from the electron linear accelerator 1. X-rays can penetrate deeply, and thereby carry out radiation processing on bigger articles. However, its efficiency is lower than electron beams since X-rays are converted by electron beams impinging on the target.

In conventional accelerator irradiating devices, the radiation is implemented by either electron beams or X-rays generated by a target hit by electron beams. The articles suitable for being irradiated by these devices are limited.

SUMMARY OF THE INVENTION

An object of the present invention is to overcome the above disadvantages of the prior arts by providing an irradiating device capable of outputting two radiation sources, both the electron beams and X-rays.

To achieve the above object, an aspect of the present invention provides an irradiating device comprising an electron accelerator, a scanning box connected to the electron accelerator, and a scanning magnet for controlling electron beams generated by the electron accelerator, wherein the scanning box is provided with both a target and an electron beam exit window, so that when the scanning magnet is not in operation, the electron beams impinge on the target and X-rays are generated to be output, and when the scanning magnet is in operation, the scanned electron beams are output via the electron beam exit window.

The target can be positioned right in a direction of the electron beams generated by the electron accelerator.

The electron beam exit window can be positioned at a left or right side of the target.

The target can be positioned at an inner side of the electron beam exit window, forming an inner target structure.

The scanning box can further be provided with a cooling fluid loop for cooling the target and the electron beam exit window.

When the scanning magnet is in operation, the scanning center of the scanned electron beams can be deflected with respect to the direction of the electron beams generated by the electron accelerator by controlling a scanning current supplied to the scanning magnet.

Another aspect of the present invention includes providing a method for controlling an irradiating device, which comprises an electron accelerator, a scanning box connected to the electron accelerator, and a scanning magnet for controlling electron beams generated by the electron accelerator, wherein the scanning box is provided with both a target and an electron beam exit window, the method comprising steps of: a) when the scanning magnet is not in operation, the electron beams impinge on the target to generate X-rays, so that the irradiating device outputs the X-rays; and b) when the scanning magnet is in operation, the scanned electron beams are deflected and pass through the electron beam exit window by supplying deflecting scanning current to the scanning magnet, so that irradiating device outputs the electron beams.

The irradiating device capable of outputting both electron beams and X-rays of the present invention has many advantages. The configuration comprising an electron accelerator, a scanning box, a target and an electron beam exit window according to the invention integrates the functions of both the existing irradiating device outputting electron beams and those outputting X-rays. When the scanning magnet is in operation, the irradiating device outputs electron beams; and when the scanning magnet is not in operation, the irradiating device outputs X-rays. Therefore, an aspect of the device of the invention is to provide a system that is capable of outputting two radiation sources of electron beams and X-rays, so as to meet requirements for radiation-processing articles with different sizes. With such a device, much more applications are supported at substantially no additional cost. On the other hand, even when the scanning magnet fails in directing the electron beams, i.e., does not work, the electron beams will travel to impinge the target to generate X-rays, without any damage to the electron beam exit window. The safety of the system is improved, which assists in increasing the life and efficiency of the irradiating device of the present invention.

These and other features, advantages and objects of the present invention will be further understood and appreciated by those skilled in the art by reference to the following specification, claims and appended drawings.

BRIEF DESCRIPTION OF THE DRAWINGS

The foregoing and/or further objects, features and advantages of the invention will become more apparent from the following description of exemplary embodiments with reference to the accompanying drawings, in which like numerals are used to represent like elements and wherein.

DETAILED DESCRIPTION OF THE PREFERRED EMBODIMENT

Figure 1:
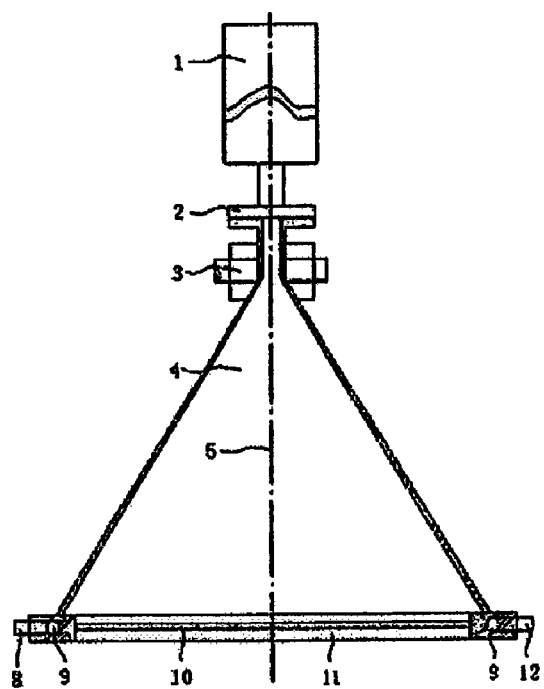
FIG. 1 is a schematic view of an existing irradiating device outputting electron beams.
Figure 2:
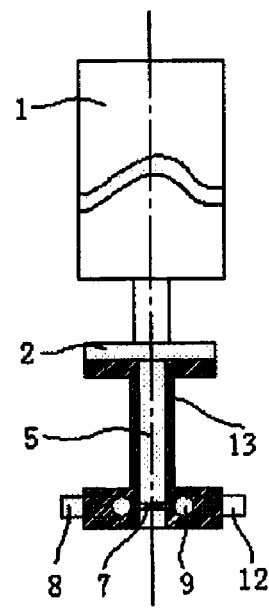
FIG. 2 is a schematic view of an existing irradiating device outputting X-rays.
Figure 3:
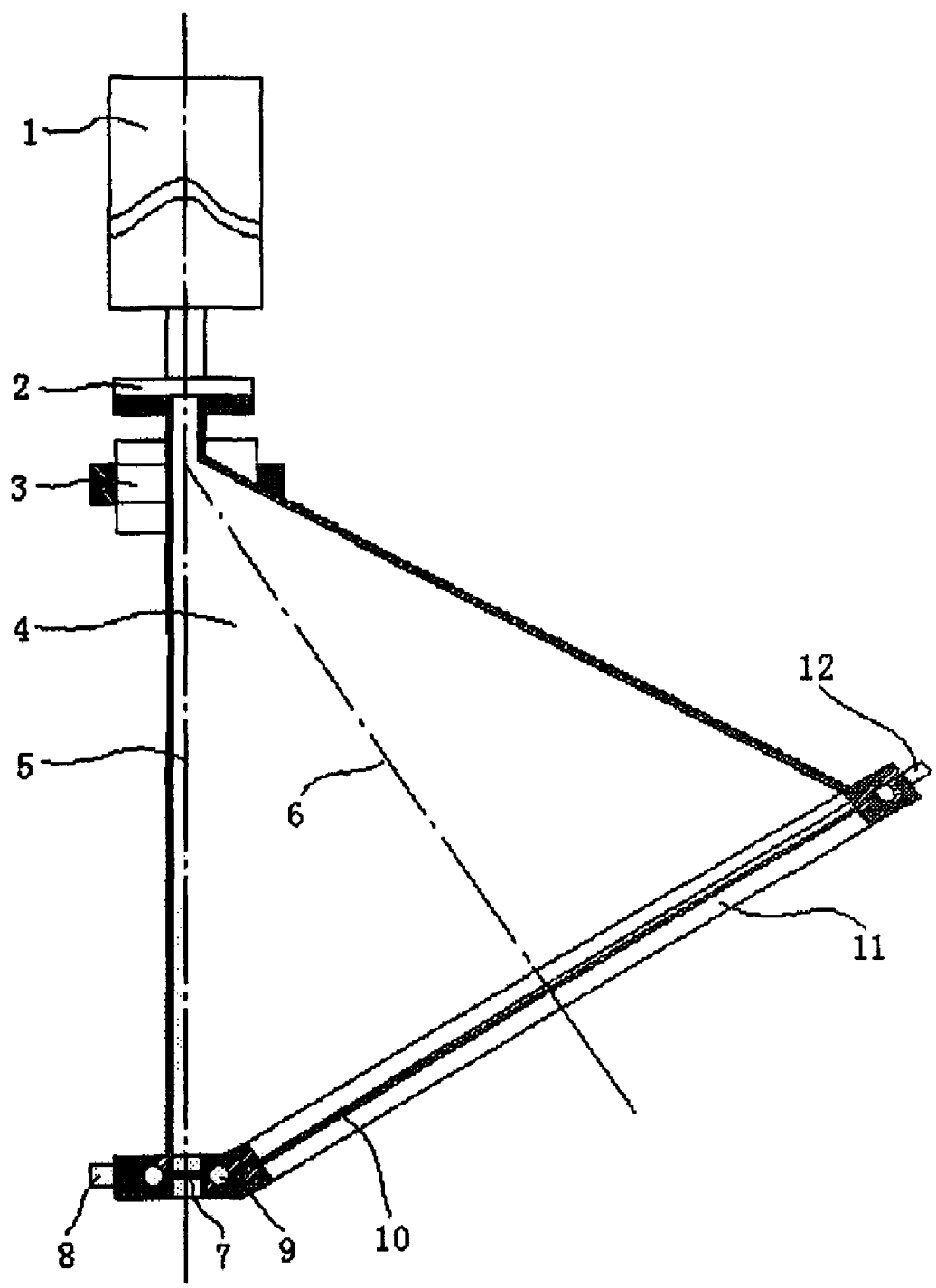
FIG. 3 is a schematic view of an irradiating device capable of outputting both electron beams and X-rays according to a first embodiment of the invention.

Referring to FIG. 3, an irradiating device capable of outputting both electron beams and X-rays according to a first embodiment of the invention includes an electron linear accelerator 1, a scanning box 4 mounted on the electron linear accelerator 1 via a flange 2, and a scanning magnet 3 mounted at a position where the scanning box 4 is connected to the electron linear accelerator 1. The scanning box 4 is provided with a target 7, made of heavy metal materials such as tungsten or tungsten alloy, right in the outputting direction of the electron linear accelerator 1, and further provided with an electron beam exit window 10, made of metallic foil such as titanium, at a left or right side of the target 7. Although the scanning box is shown in the figure in a shape of triangle, its shape is not limited and may be any suitable shape.

In the irradiating device capable of outputting both electron beams and X-rays of the invention, the scanning magnet 3 is scanning in a unidirectional manner, that is, the scanning current supplied thereto is always positive/negative. This scanning current may be obtained by superposing an original bidirectional scanning current with a positive or negative current. The target 7 is positioned right in front of the electron beams 5, while the electron beam exit window 10 is positioned right in front of the electron beams 6. The illustrated scanning box 4 is one with two different outputs from two outlets respectively. When the scanning magnet 3 is not in operation, the electron beams 5 travel in the original direction out of the accelerator, and impinge on the target 7 so as to generate X-rays, which are then output by the irradiating device. When the scanning magnet 3 is in operation, the electron beams are deflected from the direction of the electron beams 5 to be spread on one side of the beams 5, thereby forming pencil shaped electron beams 6. The electron beams 6 pass through the electron beam exit window 10 and are finally output by the irradiating device.

A cooling fluid loop 9 is provided at bottom of the scanning box 4 for cooling the target 7 and the electron beam exit window 10. The cooling fluid loop 9 is externally connected to a cooling fluid system via an inlet 8 and an outlet 12.

Figure 4:
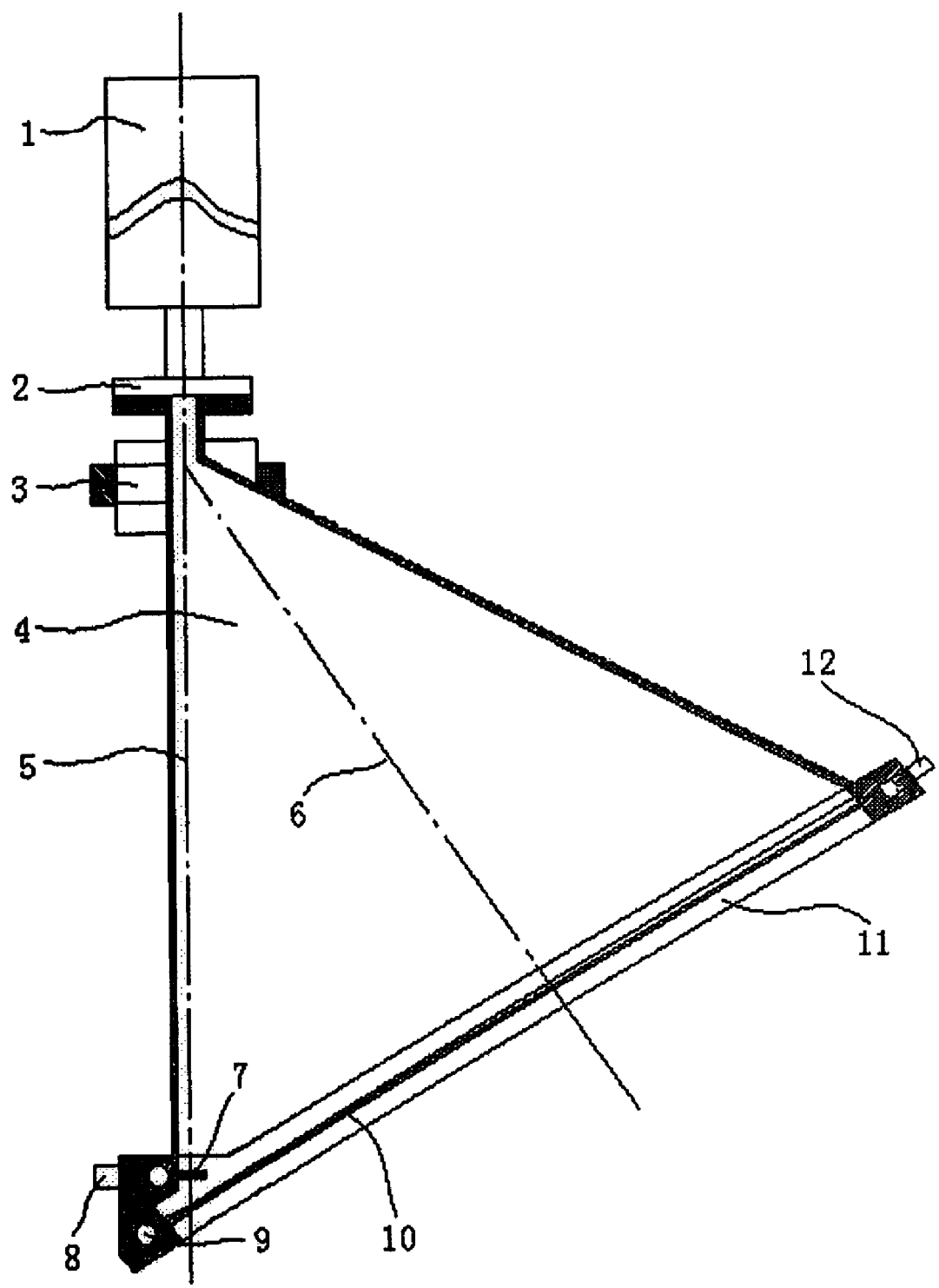
FIG. 4 is a schematic view of an irradiating device capable of outputting both electron beams and X-rays according to a second embodiment of the invention.

Referring to FIG. 4, in a second embodiment, the target 7 is provided inside the electron beam exit window 10, thus forming an inner target structure. When the scanning magnet 3 is not in operation, the electron beams 5 generated by the electron linear accelerator 1 impinge on the target 7 so as to generate X-rays, which are then output through the electron beam exit window. Here, since the electron beam exit window is very thin, for example tens of micrometers, the energy deposition of the X-rays on the electron beam exit window is so tiny that its effects can be neglected. In other words, the X-rays would not damage the electron beam exit window, which would not affect the X-rays either. When the scanning magnet 3 is in operation, the electron beams generated by the electron linear accelerator 1 are deflected from the original direction of the beams to be spread on one side of the beams 5, thereby forming a bundle of deflected electron beams 6. The electron beams 6 pass through the electron beam exit window 10 and are finally output by the irradiating device.

While some embodiments of the invention have been described above, for the illustrative purpose only, it is to be understood that the invention is not limited to the details of the illustrated embodiments, but may be embodied with various changes, modifications or improvements, which may occur to those skilled in the art without departing from the spirit and scope of the invention.

The above description is considered that of the preferred embodiments only. Modification of the invention will occur to those skilled in the art and to those who make or use the invention. Therefore, it is understood that the embodiments shown in the drawings and described above are merely for illustrative purposes and not intended to limit the scope of the invention, which is defined by the following claims as interpreted according to the principles of patent law, including the doctrine of equivalents.

The invention claimed is:

1. An irradiating device comprising:
   an electron accelerator;
   a scanning box connected to the electron accelerator; and
   a scanning magnet for controlling electron beams generated by the electron accelerator;
   wherein the scanning box is provided with both a target and an electron beam exit window, so that when the scanning magnet is not in operation, the electron beams impinge on the target and X-rays are generated to be output, and when the scanning magnet is in operation, the electron beams are scanned by the scanning magnet and then the scanned electron beams are output via the electron beam exit window.

2. The irradiating device of claim 1 wherein the target is positioned right in a direction of the electron beams generated by the electron accelerator.

3. The irradiating device of claim 2 wherein the electron beam exit window is positioned at a left or right side of the target.

4. The irradiating device of claim 2 wherein the target is positioned at an inner side of the electron beam exit window, forming an inner target structure.

5. The irradiating device of claim 1 wherein the scanning box is further provided with cooling fluid loop for cooling the target and the electron beam exit window.

6. The irradiating device of claim 1 wherein, when the scanning magnet is in operation, a center of the electron beams is deflected with respect to a direction of the electron beams generated by the electron accelerator by controlling a scanning current supplied to the scanning magnet.

7. A method for controlling an irradiating device, which comprises an electron accelerator, a scanning box connected to the electron accelerator, and a scanning magnet for controlling electron beams generated by the electron accelerator, wherein the scanning box is provided with both a target and an electron beam exit window, the method comprising steps of:
  a) when the scanning magnet is not in operation, the electron beams impinge on the target to generate X-rays, so that the irradiating device outputs the X-rays; and
  b) when the scanning magnet is in operation, the electron beams are scanned and deflected by supplying deflecting scanning current to the scanning magnet, and then the scanned electron beams pass through the electron beam exit window, so that the irradiating device outputs the electron beams.

8. The irradiating device of claim 1, wherein the electron accelerator is a linear accelerator.

9. The method of claim 7, wherein the electron accelerator is a linear accelerator.

* * * * *